(12) United States Patent
Thompson et al.

(10) Patent No.: US 7,429,485 B2
(45) Date of Patent: Sep. 30, 2008

(54) METHOD OF PRODUCING INFECTIOUS REOVIRUS

(75) Inventors: Bradley G. Thompson, Calgary (CA); Mathew C. Coffey, Calgary (CA)

(73) Assignee: Oncolytics Biotech Inc., Calgary (CA)

( * ) Notice: Subject to any disclaimer, the term of this patent is extended or adjusted under 35 U.S.C. 154(b) by 288 days.

(21) Appl. No.: 11/390,885

(22) Filed: Mar. 27, 2006

(65) Prior Publication Data

US 2006/0165724 A1      Jul. 27, 2006

Related U.S. Application Data

(60) Continuation of application No. 10/734,552, filed on Dec. 11, 2003, now Pat. No. 7,049,127, which is a division of application No. 10/337,911, filed on Jan. 8, 2003, now Pat. No. 6,703,232, which is a continuation of application No. 09/920,012, filed on Aug. 2, 2001, now Pat. No. 6,528,305.

(60) Provisional application No. 60/224,026, filed on Aug. 10, 2000.

(51) Int. Cl.
| C12Q 1/68 | (2006.01) |
| C12N 7/00 | (2006.01) |
| C12N 7/08 | (2006.01) |
| C12N 5/00 | (2006.01) |
| A61K 35/00 | (2006.01) |

(52) U.S. Cl. .................. 435/325; 435/239; 435/239.1; 435/261; 435/41; 435/42

(58) Field of Classification Search ................ 435/369, 435/239, 235; 424/215.1
See application file for complete search history.

(56) References Cited

U.S. PATENT DOCUMENTS

| 4,070,453 A | 1/1978 | Bordt et al. |
| 4,559,229 A | 12/1985 | Page et al. |
| 5,023,252 A | 6/1991 | Hsei |
| 5,658,779 A | 8/1997 | Krupey et al. |
| 6,136,307 A | 10/2000 | Lee et al. |
| 6,528,305 B2 | 3/2003 | Thompson et al. |
| 6,726,907 B1 | 4/2004 | Zhang et al. |

FOREIGN PATENT DOCUMENTS

| CA | 2283894 | 2/1999 |
| CA | 2360833 | 8/2000 |
| CA | 2407894 | 11/2001 |
| EP | 0727484 A1 | 8/1996 |
| JP | 63044532 A | 2/1988 |
| JP | 8-214876 | 8/1995 |
| WO | WO 99/08692 | 2/1999 |

OTHER PUBLICATIONS

Levin et al. Proc. Nat. Acad. Sci. 1970, vol. 66, No. 3, pp. 890-897.*
Berry et al., "Production of Reovirus Type-1 and Type-3 from Vero Cells Grown on Solid and Macroporous Microcarriers," *Biotechnology and Bioengineering* 62, (1999), pp. 12-19.
Bos, J.L., "Ras Oncogenes in Human Cancer: A Review," *Canc. Res.*, 49(17), pp. 4682-4689, (1989).
Chandron and Nibert, "Protease cleavage of reovirus capsid protein µ1 and µ1C is blocked by alkyl sulfate detergents, yielding a new type of infectious subvirion particle," *J. of Virology*, 72(1), (1998), pp. 467-475.
Coffey, M.C., et al., "Reovirus therapy of tumors with activated Ras pathway," *Science* 282, (1998), pp. 1332-1334.
Hand, et al., *J. Gen. Virol.*, 12:121-130 (1971).
Hand, et al., *J. Mol. Biol.*, 82:175-183 (1974).
Drastini, Y., et al., "Comparison of eight different procedures for harvesting avian reoviruses grown in Vero cells," *J. of Virological Methods*, 39, (1992), pp. 269-278.
Jones, R.C., et al., "Different sensitivities of Vero cells from two sources to avian reoviruses," *Research in Veterinary Science*, 48, (1990), pp. 379-380.
Joklik, W.K., et al., "Anti-thyroglobulin antibodies induced with recombinant reovirus infection in BALB/c mice," *J. Biol. Chem.*, 270:4181-4184 (1995).
Keirstead et al., "Absence of superinfection exclusion during asynchronous reovirus infections of mouse, monkey, and human cells", Virus Research, 54, 1998, pp. 225-235.
McRae, M.A. and Joklik, W.K., "The nature of the polypeptide encoded by each of the 10 double-stranded RNA segments of reovirus type 3," *Virology*, 89, (1979), pp. 578-593.
Meanger, J., et al., "Immune response to avian reovirus ain chickens and protection against experimental infection," *Aust. Vet. J.*, 75(6), (Jun. 1997), pp. 428-432.
Nwajei, B.N.C., et al., "Comparison of chick embryo liver and Vero cell cultures for the isolation and growth of avian reoviruses," *Avian Pathology*, 17, (1988), pp. 759-766.
T. Orodera et al., "Recombination Between Temperature-Sensitive and Deletion Mutants of Reovirus," *Immunology*, 71:581-585 (1990).
Poggioli, et al., *J. Virol.*, 74:9562-9570 (2000).
Smith, R.E., et al., "Polypeptide components of virions, top component and cores of reovirus type 3," *Virology*, 39, (1969), pp. 791-810.
Spandidos, D. et al., "What Reassorts When Reovirus Genome Segments Reassort?" *J. Virology*, 18:117-123 (1976).
Strong, J.E. and P.W. Lee, "The v-erbB oncogene confers enhanced cellular susceptibility to reovirus infection," *J. Virol.*, 70, (1996), pp. 612-616.
Strong, J.E., et al., "Evidence that the Epidermal Growth Factor Receptor on Host Cells Confers Reovirus Infection Efficiency Virology," 197(1), (1993), pp. 405-411.
Strong, J.E., et al., "The molecular basis of viral oncolysis: usurpation of the Ras signaling pathway by reovirus," *EMBO J.*, 17, (1998), pp 3351-3362.
Taber et al., "The selection of virus-resistant Chinese hamster ovary cells," *Cell*, 8, (1976), pp. 529-533.
Tyler, et al. ,"Reoviruses," *Encyclopedia of Virology*, 2$^{nd}$ edition, lines 4-14 on right column of p. 1456 (1999).

(Continued)

Primary Examiner—Bruce Campell
Assistant Examiner—Bao Qun Li
(74) *Attorney, Agent, or Firm*—Fish & Richardson P.C.

(57) ABSTRACT

A simple and efficient method of producing mammalian reovirus is developed using HEK 293 cells. The method provides for fast production of reovirus in high yield. Furthermore, this method provides for a simpler purification procedure of the produced reovirus.

19 Claims, No Drawings

OTHER PUBLICATIONS

Wilcox, G.E., et al., "Adaptation and characteristics of replication of a strain of avian reovirus in Vero cells," *Avian Pathology*, 14, (1985), pp. 321-328.

Wyatt R.G. et al., "Probable in vitro cultivation of human reovirus like agent of infantile diarrhoea," *Lancet* (1976) 1/7950:98-99.

2002 American Type Culture collection (ATCC) at http://www.atcc.org/Search catalogs?searchAll.cfm.

Mora, M. et al. "Association of reovirus proteins with structural matrix of infected cells", Virology 159: 265-277 (1987).

Hitt, M, et al. "Construction and propagation of human adenovirus vectors", Cell Biology vol. 1, third ed. pp. 500-512 (1998).

Barta, V.; Springer, W.T.; Millar, D.L. A comparison of avian and mammalian cell cultures for the propagation of avian reovirus WVU 2937. Avian Dis., 28(1) 216-223, 1984.

\* cited by examiner

METHOD OF PRODUCING INFECTIOUS REOVIRUS

CROSS-REFERENCE TO RELATED APPLICATIONS

This application is a continuation of U.S. application Ser. No. 10/734,552, filed Dec. 11, 2003, which is a divisional application of U.S. application Ser. No. 10/337,911, filed Jan. 8, 2003, now U.S. Pat. No. 6,703,232, which is a continuation of U.S. application Ser. No. 09/920,012, filed Aug. 2, 2001, now U.S. Pat. No. 6,528,305, which claims the benefit of U.S. Provisional Patent Application No. 60/224,026, filed Aug. 10, 2000. The entire disclosure of each of these documents is incorporated herein by reference.

FIELD OF THE INVENTION

This invention relates to a method of producing infectious mammalian reovirus which is suitable for clinical administration to mammals, including human beings.

REFERENCES

U.S. Pat. No. 5,023,252.
Berry et al., Biotechnology and Bioengineering, "Production of Reovirus Type-1 and Type-3 from Vero Cells Grown on Solid and Macroporous Microcarriers", *Biotechnology and Bioengineering* 62: 12-19 (1999).
Bos, J. L., "Ras Oncogenes in Human Cancer: A Review", *Canc. Res.* 49(17): 4682-4689 (1989).
Chandron and Nibert, "Protease cleavage of reovirus capsid protein mu1 and mu1C is blocked by alkyl sulfate detergents, yielding a new type of infectious subvirion particle", *J. of Virology* 72(1):467-75 (1998).
Coffey, M. C., et al., "Reovirus therapy of tumors with activated Ras pathway", *Science* 282: 1332-1334 (1998).
Davis, et al., *Microbiology*, Lippincott, Philadelphia (1990).
Fields, B. N. et al., *Fundamental Virology*, 3rd Edition, Lippincott-Raven (1996).
Japanese Patent 63044532A, published Feb. 25, 1988.
McRae, M. A. and Joklik, W. K., "The nature of the polypeptide encoded by each of the 10 double-stranded RNA segments of reovirus type 3", *Virology*, 89:578-593 (1979).
Nibert et al., "Reovirus and their replication", in Fields et al., *Fundamental Virology*, 3rd Edition, Lippincott-Raven (1996).
Smith, R. E., et al., "Polypeptide components of virions, top component and cores of reovirus type 3", *Virology*, 39:791-800 (1969).
Strong, J. E. and P. W. Lee, "The v-erbV oncogene confers enhanced cellular susceptibility to reovirus infection", *J. Virol.* 70: 612-616 (1996).
Strong, J. E., et al., "Evidence that the Epidermal Growth Factor Receptor on Host Cells Confers Reovirus Infection Efficiency", *Virology* 197(1): 405-411 (1993).
Strong, J. E., et al., "The molecular basis of viral oncolysis: usurpation of the Ras signaling pathway by reovirus", *EMBO J.* 17: 3351-3362 (1998).
Taber et al., "The selection of virus-resistant Chinese hamster ovary cells", *Cell* 8: 529-533 (1976).
WO99/08692A1, published Feb. 25, 1999.

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

Reovirus is a double-stranded RNA virus with a segmented genome. The receptor for the mammalian reovirus, sialic acid, is a ubiquitous molecule, therefore reovirus is capable of binding to a multitude of cells. However, most cells are not susceptible to reovirus infection and binding of reovirus to its cellular receptor results in no viral replication or virus particle production. This is probably the reason why reovirus is not known to be associated with any particular disease.

It was discovered recently that cells transformed with the ras oncogene become susceptible to reovirus infection, while their untransformed counterparts are not (Strong et al., 1998). For example, when reovirus-resistant NIH 3T3 cells were transformed with activated Ras or Sos, a protein which activates Ras, reovirus infection was enhanced. Similarly, mouse fibroblasts that are resistant to reovirus infection became susceptible after transfection with the EGF receptor gene or the v-erbB oncogene, both of which activate the ras pathway (Strong et al., 1993; Strong et al., 1996). Thus, reovirus can selectively infect and replicate in cells with an activated Ras pathway.

The ras oncogene accounts for a large percentage of mammalian tumors. Activating mutations of the ras gene itself occur in about 30% of all human tumors (Bos, 1989), primarily in pancreatic (90%), sporadic colorectal (50%) and lung (40%) carcinomas, as well as myeloid leukemia (30%). Activation of factors upstream or downstream of ras in the ras pathway is also associated with tumor. For example, overexpression of HER2/Neu/ErbB2 or the epidermal growth factor (EGF) receptor is common in breast cancer (25-30%), and overexpression of platelet-derived growth factor (PDGF) receptor or EGF receptor is prevalent in gliomas and glioblastomas (40-50%). EGF receptor and PDGF receptor are both known to activate ras upon binding to their respective ligand, and v-erbB encodes a constitutively activated receptor lacking the extracellular domain.

Since a large number of human tumors are accounted for by genetic alteration of the proto-oncogene ras or a high Ras activity, reovirus therapy is a new, promising therapy for such conditions (Coffey et al., 1998). Reovirus therapy is highly selective for Ras-associated tumor cells and leaves normal cells uninfected. Consequently, a simple and cost-effective method for the production of infectious reovirus suitable for clinical administration in human beings is needed.

Because reovirus does not pose a serious threat to human health, there has not been an intensive effort to produce reovirus efficiently. The mammalian reovirus is traditionally grown in mouse L-929 fibroblasts (Nibert et al., 1996). It has also been reported to grow in Chinese hamster ovary cells and Vero cells, an African green monkey kidney cell line (Taber et al., 1976; Davis et al., 1990). In addition, a primary culture of swine kidney was used to culture a swine reovirus (Japanese Patent 63044532A, published Feb. 25, 1988). In a study aiming at mass production of the reovirus, Berry et al. conducted an investigation of the optimal methods of culturing Vero cells and the subsequent reovirus infection (Berry et al., 1999). Vero cells were grown in either Cytodex-1 or Cultispher-G microcarriers, and culture parameters such as cell density, time course of viral growth and the ratio of cells to beads in the microcarrier were varied and virus yield determined. The study showed that the yield of virus varied greatly with the culture parameters, and complicated culture conditions (e.g. cell number per beads relative to multiplicity of infection) were required to obtain reasonable yield. Therefore, there remains a need for a simple, efficient method to produce clinically useful reovirus.

SUMMARY OF THE INVENTION

The present invention is directed to a simple and efficient method of producing reovirus by culturing reovirus in human embryo kidney 293 (HEK 293) cells. The yield in HEK 293 cells is unexpectedly high, particularly in comparison to previous work using L-929 cells or Vero cells. Moreover, by using the present invention, a high yield is achieved early in the course of infection, before viral particles are released from the cells. Therefore, the virus can be harvested early from intact cells, allowing the virus to be purified in the absence of the culture media. This makes the purification procedure relatively simple.

Accordingly, one aspect of the invention provides a method of producing mammalian reovirus, comprising the steps of contacting HEK 293 cells with a mammalian reovirus under conditions which result in reoviral infection of said HEK 293 cells; incubating the culture of said infected cells for a period of time sufficient to allow for viral replication; and harvesting the virus produced.

Any mammalian reovirus can be produced using this method. In particular, human reovirus for clinical administration in human beings can be produced using this method. Most particularly, reovirus serotype 3 and the Dearing strain are produced. Other mammalian reovirus can be produced efficiently by the presently claimed method as well.

Another feature of the invention is that because reovirus is produced rapidly in the HEK 293 cells, this invention provides for a fast and cost-effective method of producing reovirus. Also, since virus titer in the HEK 293 cell culture is high before the cells are completely lysed, the virus may be harvested when it is still associated with the cell, hence the purification procedure of the virus can be relatively simple, further reducing the cost of production. Therefore, this invention provides for a method wherein the virus is harvested before all the cells are lysed. Preferably, the virus is harvested when 20-95% of the cells remain viable, more preferably 35-90%, and most preferably 50-80%.

Another aspect of the invention is that a wide range of multiplicity of infection may be used to achieve virus production. Although a multiplicity of infection of 0.1 is sufficient, higher multiplicities can be used to shorten the production time, e.g., a multiplicity of up to 10. Preferably a multiplicity of infection of less than 1 is used, more preferably at or around 0.5.

Another aspect of the invention provides for a method of producing reovirus in both adherent and suspension cell cultures, since HEK 293 cells can be adapted to grow in both kinds of cultures. HEK 293 cells which have been adapted for other purposes or culture conditions, or transformed with an exogenous DNA, are also useful in the present invention.

The present invention also provides for a mammalian reovirus composition which is prepared by the methods described above. This composition may preferably be purified. The composition is suitable for extended storage, e.g. by freezing. The composition is useful to treat tumors or other cell proliferative disorders caused by an activated ras pathway, and is suitable for administration in human beings because HEK 293 cells are approved for growing biological products by the Food and Drug Administration. The composition can further comprise a pharmaceutically acceptable carrier or excipient, and/or a therapeutical agent which can be used along with the reovirus for its intended purposes.

DETAILED DESCRIPTION OF THE INVENTION

The present invention is directed to a method of producing mammalian reovirus by using human embryo kidney 293 (HEK 293) cells. We found that HEK 293 cell are a more efficient host cell for reovirus than L-929 cells or Vero cells. Although never reported to support reovirus replication before, HEK 293 cells produced more reovirus in a shorter time course than L-929 cells or Vero cells. Consequently, by using HEK 293, production costs can be lowered. Moreover, because the reovirus is still associated with HEK 293 cells when the titer is sufficiently high, a relatively simple procedure may be used to purify the virus and further lower the production cost.

Prior to describing the invention in further detail, the terms used in this application are defined as follows unless otherwise indicated.

Definitions

As used herein, "HEK 293 cells" refer to the human embryo kidney cell line designated 293 (ATCC Number CRL-1573) or its derivatives. For example, 293/SF cells (ATCC Number CRL-1573.1) are HEK 293 cells which have been adapted to grow in serum-free media. Also contemplated in this invention are HEK 293 cells adapted to grow in other culture conditions, or any kind of HEK 293 cells or derivatives which are transformed with an exogenous DNA, provided that this transformation does not impair the ability of the cells to support efficient reovirus production as described in this invention.

As used herein, "reovirus" refers to any virus classified in the reovirus genus, whether naturally occurring, modified or recombinant. Reoviruses are viruses with a double-stranded, segmented RNA genome. The virions measure 60-80 nm in diameter and possess two concentric capsid shells, each of which is icosahedral. The genome consists of double-stranded RNA in 10-12 discrete segments with a total genome size of 16-27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (see, for example, Fields, B. N. et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, 1998). For example, the virion may be treated with chymotrypsin in the presence of micelle forming concentrations of alkyl sulfate detergents to generate a new infectious subvirion particle.

The reovirus may be a recombinant (i.e. reasserted) reovirus from two or more types of reoviruses with differing pathogenic phenotypes such that it contains different antigenic determinants, thereby reducing or preventing an immune response by a mammal previously exposed to a reovirus subtype. Such recombinant virions can be generated by co-infection of mammalian cells with different subtypes of reovirus with the resulting resorting and incorporation of different subtype coat proteins into the resulting virion capsids.

As used herein, "contacting" a cell with a virus refers to placing the virus in the culture of the cell such that the virus has the opportunity to make a contact with the cell, which may lead to successful infection by the virus.

As used herein, "viral infection" refers to the entry of a virus into a cell and the subsequent replication of the virus in the cell.

As used herein, "multiplicity of infection" refers to the ratio of the number of virus to the number of cells when a virus is used to contact cells.

As used herein, "cell lysis" refers to the disruption of cell membrane of a cell and the subsequent release of all or part of the content of the cell.

As used herein, "complete lysis" refers to the lysis of every cell in a culture of multiple cells.

As used herein, "culture conditions" refer to the conditions used in a cell culture, including but not limited to the temperature, type of culture containers, humidity, concentration of $CO_2$ or any other gas used in the culture containers, type of the culture medium, the initial density of the cultured cells, and if the cells are infected with a virus, the initial multiplicity of infection.

As used herein, a virus that is "cell associated" refers to a virus which is attached to or trapped in part of a cell in which the virus has been produced. Thus, a virus is cell associated before the host cell is lysed. When cell lysis begins, a virus may be still attached to or trapped in part of the broken cell and remain cell associated. However, when the virus is released free into the medium, it is not cell associated anymore.

As used herein, a cell is "disrupted" when the cell membrane is ruptured and at least some of the cell content is released from the cell. A cell may be disrupted, for example, by freeze-thawing, sonication or detergent treatments.

As used herein, "harvest" the virus refers to the act of collecting the produced virus from a cell culture which has been previously infected with the virus. Harvesting of the virus may involve breaking up the host cell if the virus is still cell associated. Alternatively but less preferably, viral particles which have been released into the culture media can be harvested from the media.

As used herein, "cytopathic effect" is indicated by the cells becoming swollen and granular in appearance and the cell clumps breaking up. The cells which show a cytopathic effect stain negative in a viable cell count because they will take up the staining dye.

As used herein, "adherent cells" refer to cells which adhere to the culture containers in a cell culture. Examples of adherent cells include monolayer cells, which are cells that form a single layer of cells on the surface of a culture container. "Suspension cells" or "suspended cells" refer to cells which do not adhere to culture containers in a cell culture. Suspension cells can be grown in a "spin culture", which is a culture in which the culture medium is stirred continuously during the culture process.

As used herein, "viability of the cells" or "percentage of cells remaining viable" is the percentage of the cells which do not show a cytopathic effect in a population.

As used herein, "harvest time" refers to the time point at which the reovirus is collected and purified. The virus is preferably harvested when titer is sufficiently high and the virus is still cell-associated. Although the virus may be harvested even after complete cell lysis has occurred, it is desirable to harvest the virus before it is released from the cells to simplify the purification process. Thus, viability of the cells is routinely measured as an indication of whether the virus is still cell-associated. The virus is generally harvested when at least 5% of the cells are viable. Preferably, the virus is harvested when 20-95% of the cells are viable, more preferably when 35-90% cells remain viable, and most preferably when 50-80% cells remain viable.

Methods

Normal cells are generally not susceptible to reovirus infection, and cultured cell lines vary to a great extent in their ability to support reovirus production. In our attempt to develop an efficient host cell to produce reovirus, a variety of cells were employed and HEK 293 cells proved to be very efficient. In a typical experiment (Example 1), HEK 293, Vero and L-929 cells were grown to confluency and infected with the reovirus at a multiplicity of infection (m.o.i.) of 1. The yield of virus was determined at various time post infection. Surprisingly, HEK 293 cells, which have not been reported to support reovirus growth, produced almost 50 times more reovirus at 24 hours post infection than L-929 cells, which are routinely used to culture mammalian reovirus. Vero cells produced even less reovirus at this point, yielding 3000 times less reovirus than the HEK-293 cells.

At 36-48 hours post infection, the virus yield in the HEK-293 cells began to plateau, but the titer was still one order of magnitude higher than the titer produced in L-929 cells and two orders of magnitude higher than that of Vero cells. It was not until 96 hours post infection that all three cells lines produced about the same titer of reovirus, at $10^9$ to $10^{10}$ per milliliter.

These results indicate that the HEK-293 cell is a very efficient system for the production of reovirus, allowing for shortened production time which will markedly reduce the cost of production.

To further optimize the HEK 293 cell production conditions, reovirus was used to infect the HEK 293 cells at various m.o.i., and the yield was determined (Example 2). The results suggest that a lower m.o.i. is even more advantageous. Thus, at 48 hours post infection, the cells which were inoculated at a m.o.i. of 0.5 produced more than $10^{10}$ viruses per ml, which was the maximal yield at these culture conditions. After this point, the titer went down by about two fold, and reached the maximal yield again at 96 hours. A similar pattern was observed for the culture with an initial m.o.i. of 0.1. Although the reason is not clear, it is possible that the decrease at 72 hours is caused by proteolytic degradation of the virus. This is apparently followed by replication to produce the higher yield at 96 hours.

Consequently, the best time to harvest reovirus under these culture conditions is 36-60 hours post infection. At this period of time, the titer is high, and the virus is still associated with the cell fragments and membranes, which makes purification of the virus relatively simple. At 96 hours, all the cells have lysed and the virus is released into the media along with the degradation products of the dead cells, making purification much more complicated than when the virus is cell associated.

For best efficiency, the virus should be harvested when the yield is sufficiently high but most of the virus is still associated with the cells. The harvest time should be determined empirically when culture conditions are varied. To determine if the virus is associated with the cells, a small aliquot of the culture can be examined, e.g., under the microscope, to determine the degree of cell viability at different time points after infection. Alternatively, a viable stain can be conducted to determine the percentage of viable cells. To simplify the purification process, the virus is typically harvested before all the cells have been lysed. Preferably, the virus is harvested when 20-95% of the cells remain viable. More preferably, the virus is harvested when 35-90%, and most preferably 50-80%, of the cells remain viable.

HEK 293 cells are adherent cells and can be grown in cell culture flasks, roller bottles, microcarrier systems or hollow fiber systems, or any other system that is suitable for growing adherent cells. HEK 293 cells may be modified to generate derivative cells. For example, the 293/SF cell (ATCC Number CRL-1573.1) was derived from the HEK 293 cell and adapted to serum-free culture conditions. The 293/SF cells grow as a mixture of adherent and suspension cells and may be grown in any of the culture containers described above, as well as spinner bottles, stirred vessels (fermenters), hollow fiber systems, or any other culture containers suitable for suspension cells.

In order to produce industrial amounts of reovirus, 293/SF cells were cultured in 15 L spinner flasks and infected with reovirus at a multiplicity of infection of 0.5 when cell density reached $10^6$/ml. The culture was incubated until cell lysis began, as evidenced by the culture media color change from red to orange due to the presence of Phenol Red in the media, or by a viable cell count under the microscope. At this point, the virus was harvested by centrifugation. The virus was then purified as described in Materials and Methods and used in clinical administrations or stored for future use. For storage, the virus can be frozen or lyophilized according to methods established in the art, with or without stabilizing agents.

Reovirus Compositions

Reovirus compositions may be prepared using reovirus produced by the methods described above. The compositions are suitable for clinical administration in mammals, including human beings. When used for clinical administrations, the compositions are preferably purified. Human reovirus, particularly serotype 3, most particularly strain Dearing, is the preferred composition prepared by the methods of this invention. However, other mammalian reovirus may be produced as well.

This invention also includes pharmaceutical compositions which contain one or more of the reoviruses, made according to the present application, associated with "pharmaceutically acceptable carriers or excipients". In making the compositions of this invention, the active ingredient/reovirus is usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient/reovirus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the reovirus of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

CI=Confidence Interval
$TCID_{50}$=Tissue Culture Infectious $Dose_{50}$
μM=micromolar
mM=millimolar
M=molar
ml=milliliter
μl=microliter
mg=milligram
μg=microgram
g/L=grams per liter
rpm=revolutions per minute
FBS=fetal bovine serum
DTT=dithiothrietol
NP-40=Nonidet P-40 (Octylphenoxy Polyethoxy Ethanol)
SDS=sodium dodecyl sulfate
PBS=phosphate buffered saline
β-ME=β-mercaptoethanol
MOI or m.o.i.=multiplicity of infection
PFU=plaque forming units
hr=hour
° C.=degree Celsius General Method Cells and Virus Human embryo kidney 293 (HEK 293), Vero (African green monkey kidney) cells, and mouse fibroblast L-929 cells were provided by the manufacturer BioReliance Corporation (Rockville, Md.). HEK 293 cells were grown in a culture medium containing 10% heat-inactivated horse serum and 90% of the following mixture: Eagle's minimum essential medium with 2 mM L-glutamine and Earle's Balanced Salt Solution adjusted to contain 1.5 g/L sodium bicarbonate, 0.1 mM non-essential amino acids, and 1.0 mM sodium pyruvate. Mouse L-929 and Vero cells were propagated in a culture medium containing 10% FBS and 90% of the following mixture: Eagle's minimum essential medium with 2 mM L-glutamine and Earle's Balanced Salt Solution adjusted to contain 1.5 g/L sodium bicarbonate, 0.1 mM non-essential amino acids, and 1.0 mM sodium pyruvate.

The 293/SF cells were grown in 293 Serum Free Medium (Life Technologies, Rockville, Md.) supplemented with 4 mM L-glutamine at 36° C.±2° C., 6%±2% $CO_2$ and 80%±5% relative humidity in spinner flasks at an impeller speed of 35-40 rpm.

The Dearing strain of reovirus serotype 3 used in these studies was propagated in suspension cultures of L-929 cells purified according to Smith (Smith et al., 1969) with the exception that β-mercaptoethanol (β-ME) was omitted from the extraction buffer. Reovirus labelled with [$^{35}$S]-methionine was grown and purified as described by McRae and Joklik (McRae and Joklik, 1979). The particle/PFU ratio for purified reovirus was typically 100/1.

Infection of Monolayer Cells and Quantitation of Virus

Confluent monolayers of HEK 293, Vero, and L-929 cells were grown in 24-well plates and infected with a reovirus at known multiplicities of infection. After 1 hr incubation at 37° C., the monolayers were washed with warm media and then incubated in their culture medium. At various time points postinfection, a mixture of NP-40 and sodium deoxycholate was added directly to the media on the infected monolayers to final concentrations of 1% and 0.5%, respectively. The lysates were then harvested and virus yields were determined by plaque titration on L-929 cells and expressed as $Log_{10}TCID_{50}$/ml.

Infection of Suspension Cells and Purification of Virus

293/SF cells were grown to $10^6$/ml and infected with the reovirus. The culture was allowed to grow until the color of the medium turned from red to orange, or until the viability of the cells dropped to the desired level as evidenced by a viable cell count. Viable cell counts can be performed under the microscope for cells that do not show a cytopathic effect, which is indicated by the cells becoming swollen and granular in appearance and the cell clumps breaking apart. Viable cell counts can also be performed by a viable stain as commonly used in the art. When the desired cell viability level was reached, the cells were pelleted in a centrifuge and resuspended in 10 mM Tris, pH 7.4, 250 mM NaCl and 0.1% Triton X-100.

The cells were then lysed by freeze-thawing and kept on ice for 20-40 minutes with periodical vortexing to mix and lyse the cells. The suspension was extracted with an equal volume of pre-chilled Freon® (1,1,2-trichloro-1,1,2-trifluoroethane) by vortexing for 10 minutes, followed by centrifugation at 2500 rpm for 10 minutes at 4° C. to separate the difference phases. The aqueous (top) phase was removed and re-extracted twice as described above. After the final extraction, the aqueous layer was transferred to a fresh tube, and Triton X-100 was added to a final concentration of 0.5%.

The virus was purified by a cesium chloride step gradient. The gradient contained two layers of CsCl solutions (1.20 g/ml and 1.4 g/ml, respectively) prepared in 10 mM Tris (pH 7.4). The virus suspension was loaded on top of the gradient and centrifuged in a SW 28.1 rotor at 26,000 rpm for 2 hours at 4° C. The viral band (the lower of the two bands because the upper band contained empty capsids) was harvested and dialyzed against sterile PBS.

Example 1

Determination of Optimal Cell Lines for the Production of Reovirus

To determine whether there were differences between susceptible cell lines in the amount of reovirus produced as a consequence of infection, a number of different cell lines that exhibited reovirus susceptibility were assayed for relative amount of reovirus produced. Of particular interest were those cell lines that had been approved by various regulatory authorities for the production of a biological agent. Accordingly, HEK 293, Vero, and L-929 cells were exposed to reovirus, and their ability to produce reovirus was compared.

Quantitation of viral production was accomplished by harvesting infected cells and their growth media at various time points post infection. The lysates produced were subsequently subjected to plaque titration analysis to determine the viral yield, which is expressed as titer ±95% CI ($Log_{10}TCID_{50}$/ml) in Table 1 below. The results indicate that, whereas all of the tested cells were susceptible to reovirus infection, there were considerable differences in the amount of virus produced in each of these cells lines.

TABLE 1

Time Course of Viral Yield of Various Cell Lines
(expressed as titer ± 95% CI in $Log_{10}TCID_{50}$/ml)

| TIME | HEK 293 | Vero | L929 |
|---|---|---|---|
| 24 HOURS | 8.30 ± 0.51 | 4.80 ± 0.35 | 6.68 ± 0.24 |
| 36 HOURS | 9.05 ± 0.43 | 5.55 ± 0.32 | 7.93 ± 0.40 |
| 48 HOURS | 9.55 ± 0.49 | 6.68 ± 0.40 | 8.55 ± 0.49 |
| 72 HOURS | 9.30 ± 0.43 | 8.18 ± 0.36 | 9.05 ± 0.32 |
| 96 HOURS | 9.80 ± 0.35 | 9.93 ± 0.59 | 9.30 ± 0.43 |

The results show clearly that the amounts of virus produced were highest in the HEK 293 cells. Further, the HEK 293 cells produced more virus earlier, allowing for shortened production times for the manufacture of the reovirus.

Example 2

Effect of Starting Multiplicity of Infection on Final Viral Production

To determine whether the starting multiplicity of infection determines final viral output, HEK 293 cells were infected with a range of starting multiplicities of infection (m.o.i.) between 1 and 0.1. Our results, shown in Table 2, indicate that there is indeed a relationship between the starting m.o.i. and the final viral production. A starting m.o.i. of less than 1 is optimal for the large scale manufacture of reovirus.

TABLE 2

Effect of M.O.I. on Viral Production
(expressed as titer ± 95% CI in $Log_{10}TCID_{50}$/ml)

| TIME | 1.0 MOI | 0.5 MOI | 0.1 MOI |
|---|---|---|---|
| 24 HOURS | 9.18 ± 0.36 | 8.55 ± 0.43 | 7.68 ± 0.24 |
| 36 HOURS | 8.92 ± 0.52 | 9.30 ± 0.43 | 9.37 ± 0.48 |
| 48 HOURS | 9.55 ± 0.43 | 10.30 ± 0.37 | 9.68 ± 0.50 |
| 72 HOURS | 9.55 ± 0.32 | 9.93 ± 0.40 | 9.18 ± 0.40 |
| 96 HOURS | 9.80 ± 0.00 | 10.30 ± 0.43 | 10.18 ± 0.36 |

Furthermore, our results demonstrate that there is also an optimal time at which to harvest the cells, which will be important. We found that viral production is greatest after 24 hours. This is not surprising as prior to 24 hours, there would be insufficient time for adequate viral protein synthesis and the assembly of the mature virion. More surprising is the observation of a decrease in virus quantity at the 72 hour point followed by a marked increase in the number of infectious particles at the 96 hour time point. It is presumed that this slight decrease at 72 hours is likely due to proteolytic degradation of the virus followed by a second round of virus replication at the 96 hour point.

We claim:

1. A method of purifying reassorted reovirus from cells, comprising the step of harvesting the reassorted reovirus from reassorted reovirus-infected human embryo kidney 293 (HEK 293) cells before all the reassorted reovirus-infected HEK293 cells are lysed by the reassorted reovirus.

2. The method of claim 1 wherein the reassorted reovirus is harvested when the reassorted reovirus-infected HEK293 cells are viable in an amount selected from the group consisting of at least 5%, 20-95%, 35-90% and 50-80%.

3. The method of claim 1 wherein the reassorted reovirus-infected HEK293 cells are adherent cells.

4. The method of claim 1 wherein the reassorted reovirus-infected HEK293 cells are in suspension.

5. The method of claim 1 wherein the harvesting step comprises separating the cells from the culture media, disrupting the cells to release the reassorted reovirus from the cells, and purifying the reassorted reovirus.

6. The method of claim 5 wherein the cells are separated from the culture media by centrifugation and disrupted by freeze-thawing, and the reassorted reovirus is purified by a CsCl gradient.

7. The method of claim 1, further comprising the step of freezing the harvested reassorted reovirus for storage.

8. The method of claim 7 wherein the harvested reassorted reovirus is stored at −60° C. or below.

9. The method of claim 1 further comprising the step of lyophilizing the harvested reassorted reovirus for storage.

10. The method of claim 1 wherein the multiplicity of infection in step (a) is selected from the group consisting of 10 or less, 5 or less, 1 or less, 0.5, and 0.1.

11. The method of claim 1, further comprising preparing the reassorted reovirus-infected HEK293 cells by (a) contacting a culture of HEK 293 cells with a reassorted reovirus under conditions which result in reoviral infection of the HEK 293 cells and (b) incubating the culture of said infected cells for a period of time sufficient to allow for viral replication, thereby producing the reassorted reovirus-infected HEK293 cells.

12. The method of claim 1, further comprising preparing the reassorted reovirus-infected HEK293 cells by (a) contacting HEK 293 cells with at least two different reoviruses under conditions which result in reoviral infection of said HEK 293 cells and (b) incubating the culture of said infected cells to allow reassortment of the reoviruses to occur, thereby producing the reassorted reovirus.

13. The method of claim 1 wherein the reassorted reovirus is a result of reassortment including a mammalian reovirus.

14. The method of claim 13 wherein the mammalian reovirus is a human reovirus.

15. The method of claim 14 wherein the human reovirus is selected from the group consisting of the Lang strain, the Jones strain, the Dearing strain and the Abney strain.

16. The method of claim 15 wherein the human reovirus is a serotype 3 reovirus.

17. The method of claim 15 wherein the human reovirus is the Dearing strain.

18. The method of claim 1 wherein the reassorted reovirus is a result of reassortment between reoviruses of different subtypes.

19. The method of claim 18 wherein the reassorted reovirus is a result of reassortment between reoviruses selected from the group consisting of the Lang strain, the Jones strain, the Dearing strain and the Abney strain.

* * * * *